United States Patent [19]
Imbert

[11] Patent Number: 5,338,309
[45] Date of Patent: Aug. 16, 1994

[54] SYRINGE HAVING TWO COMPONENT BARREL

[75] Inventor: Claude Imbert, La Tronche, France

[73] Assignee: Becton, Dickinson and Company, Franklin Lakes, N.J.

[21] Appl. No.: 918,720

[22] Filed: Jul. 21, 1992

[51] Int. Cl.$^5$ ............................................. A61M 5/00
[52] U.S. Cl. ................................. 604/187; 604/227; 604/110
[58] Field of Search ............... 604/187, 218, 227, 232, 604/199; 206/570, 571, 365

[56] References Cited

U.S. PATENT DOCUMENTS

| | | | |
|---|---|---|---|
| 2,047,512 | 7/1939 | Kauffman | 604/227 |
| 2,678,647 | 5/1954 | Bruger | 604/227 |
| 3,987,990 | 10/1976 | Tischlinger | 604/227 X |
| 4,068,661 | 1/1978 | Hennings | 604/227 |
| 4,840,616 | 6/1989 | Banks | 604/110 |
| 4,878,903 | 11/1989 | Mueller | 604/199 |
| 4,909,788 | 3/1990 | Egolf | 604/187 |

FOREIGN PATENT DOCUMENTS

| | | | |
|---|---|---|---|
| 773091 | 10/1971 | Belgium | 604/227 |
| 20266 | 12/1929 | Netherlands | 604/227 |

*Primary Examiner*—C. Fred Rosenbaum
*Assistant Examiner*—Vanitha Alexander
*Attorney, Agent, or Firm*—Arthur D. Dawson

[57] ABSTRACT

A syringe assembly comprising a barrel having a hollow cylindrical shaped body. The body has a proximal first portion with an adjacent second portion which includes a circumferential groove for mounting a finger flange. The barrel has a third portion adjacent to the second portion. The body has a distal tip with a passage therethrough for mounting a needle in fluid communication with the bore. The finger flange has an opening with a diameter defined by a plurality of inwardly facing cantilevers. The diameter of the flange opening is less than that of the body first portion and third portion, requiring a deflection of the cantilevers when the flange is moved over the first portion to the second portion by an installation force. The flange is retained by the barrel through interaction between the inwardly facing cantilevers and the circumferential groove. The design of the cantilevers and the barrel proximal first and second portions provides that a force for removal of the finger flange is greater than the installation force.

8 Claims, 4 Drawing Sheets

SYRINGE HAVING TWO COMPONENT BARREL

BACKGROUND OF INVENTION

1. Field of the Invention

This invention relates to syringes and more particularly to syringes with a finger flange attached to a barrel.

2. Description of Related Information

Generally speaking, a hypodermic syringe consists of a cylindrical barrel, most commonly made of a thermoplastic material or glass, having a distal end connected to a sharp needle or adapted to be connected to a hypodermic needle assembly, a proximal open end having an external finger flange and internally adapted to receive a resilient stopper.

In many cases, the finger flange is integrally formed with the barrel. The process of integrally forming the flange and the barrel limits the design of the flange, particularly in the case of a glass barrel formed from glass tubing. Further, the need to provide sufficient strength for the flange requires the proximal end of the barrel portion to be larger than would be required to accommodate only the volume. This o additional size may affect the ability of the syringe to be fit into syringe pumps.

In the case of syringes intended for prefilling and subsequent use as a package for a medicament, the presence of a fixed flange constrains the design of the processing and filling apparatus. Further, the presence of a fixed flange may make the barrel more prone to breakage during the processing and filling operations.

Syringes have been in use for many years. Several early designs of syringes have had flanges formed from materials other than glass and subsequently attached to the barrel by clamping, threading or the like. Patents exemplary of these types of devices are described below.

U.S. Pat. No. 801,912 to Rehmann shows a glass syringe barrel with a proximal rim and a metal finger flange apparently put on from the distal end of the barrel and slid proximally to engage the rim. The metal flange is held against the rim by an internal flat spring compressed against the barrel.

U.S. Pat. No. 1,142,682 to Dickinson teaches a separate flange installed over the distal end of the syringe and slid proximally along the barrel to a proximal rim. The flange includes a spring which serves to hold the collar with the flange against the barrel's proximal rim and also maintains tension against the plunger.

U.S. Pat. No. 1,798,116 to Brockway teaches a two part finger flange which has a threaded collar containing the flange placed over the distal end of the syringe, then slid upwardly to the proximal end of the syringe. A threaded plug is then inserted into the proximally placed threaded collar on top of a swedging ring and tightened down to hold the flange in position at the proximal end of the barrel.

U.S. Pat. No. 4,112,945 to Helixon et al. teaches a syringe designed to receive a prefilled cartridge which has threaded cap with radially extending arms to provide finger holds. When the cap is threaded onto the barrel containing the cartridge, the cap serves to retain the cartridge and provide the finger holds.

U.S. Pat. No. 4,469,482 to Lissenberg et al. teaches a disposable syringe having a finger grip connected around the barrel according to the "so-called snap-cap principle." This device apparently comprises a planar flange with a central extended collar to fit around and over the proximal end of the syringe. There is no teaching in the specification of the structure of the "so-called snap cap", however, FIG. 1, element 16 apparently shows a semicircular projection on the cap in apparent conjugation with a recess on the proximal end of the barrel.

U. S. Pat. No. 4,792,329 to Schreuder teaches a syringe in which the cylindrical body is an ampoule having closures at each end. The proximal closure functions as a plunger stopper after attachment of a plunger rod. A finger grip is mounted on the out side of the ampoule by the "so-called snap cap principle." '329 teaches that the finger grip is preferably manufactured from a slightly resilient but non-deformable material, for example a synthetic. '329 also teaches another embodiment where the finger grip forms are one assembly with the ampoule and may then be formed as a flange-like part of the ampoule projecting radially outwards.

British Patent Specification 1,479,536 to Lissenberg et al. teaches a finger grip consisting of a tensioning collet which is clamped around the end of the barrel by means of a tensioning sleeve. The patent teaches a finger grip preferably of slightly resilient material for example plastic.

While the art presented above shows several different forms of finger flanges made from metal, glass and plastic, most of the devices taught are multi-component, are applied from the distal end of the barrel and slid to the proximal side. In most of these prior art examples, the assembly of the finger flange requires a complex assembly procedure, a fitting on, a sliding together, a threading and a tightening. In some of the examples a hoop stress or compression is exerted upon the barrel by the flange assembly. Such a stress would be exacerbated by out-of-roundness conditions which would tend to concentrate the stress. This stress may lead to distortion or cracking of the barrel, particularly when the barrel is glass.

Thus, in the field of syringes with finger flanges, there still exists a need for a simple to manufacture syringe assembly having as a design feature a finger flange with a higher force for removal than the force for assembly. The higher removal force provides functional utility while the lower installation force provides easy assembly.

SUMMARY OF THE INVENTION

A syringe assembly of the present invention includes a hollow cylindrically shaped barrel defining a bore, an external side, an internal side, a distal end and a proximal end, the proximal end being open to accept a plunger assembly slidably within the bore. On the external side of the barrel at the proximal end, there is a first portion. Adjacent to the first portion is a second portion including a circumferential groove for mounting a finger flange and adjacent to the second portion is a third portion. The circumferential groove defines a diameter smaller than the diameters of the first and third portions. The barrel has a tip, having a passage therethrough, at its distal end for accepting a needle in fluid communication with the bore of the barrel. The finger flange has an opening. The diameter of the finger flange opening is defined from two components, a plurality of inwardly facing cantilevers and spaces between the cantilevers. The flange is held by the barrel so that the cantilevers are at least partially positioned in the circumferential groove. The flange opening diameter is smaller than the diameters of the first portion and the third portion of the barrel. The force for placement of the flange on the barrel is less than the force for removal of the flange from the barrel. The flange can be designed to couple with a complementary structure on an apparatus.

DETAILED DESCRIPTION OF THE DRAWINGS

Figure 1:
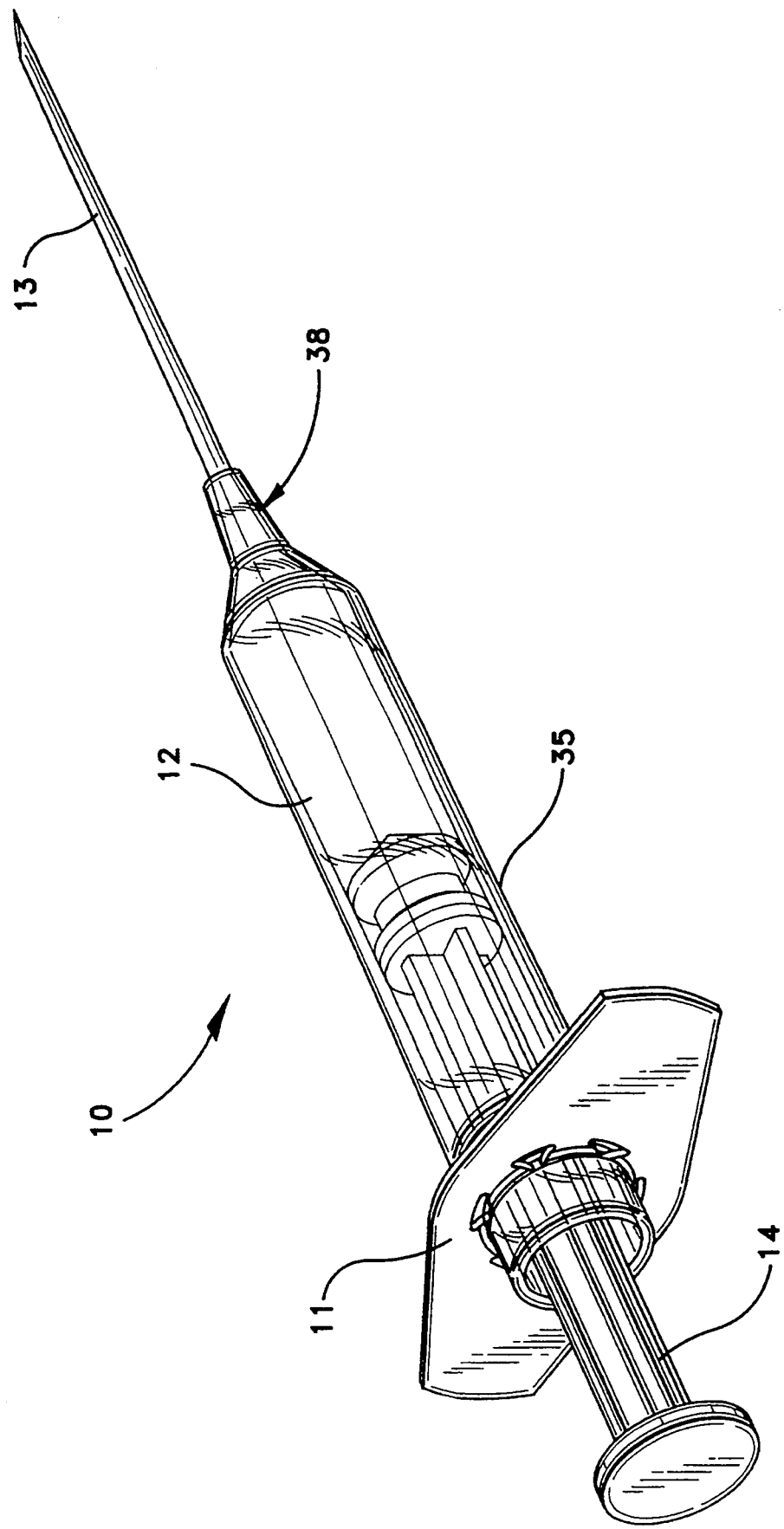
FIG. 1 is a perspective view of the syringe assembly of the present invention.

While this invention is satisfied by embodiments in many different forms, there is shown in the drawings and will be herein be described in detail preferred embodiments of the invention with the understanding that the present disclosure is to be considered exemplary of the principles of the invention and is not intended to limit the invention to the embodiments illustrated. The scope of the invention will be measured by the appended claims and their equivalents.

Adverting to FIGS. 1–4c, an operable syringe assembly 10 comprises a barrel 12, a needle assembly 13, a plunger assembly 14 and a finger flange 11.

Figure 2:
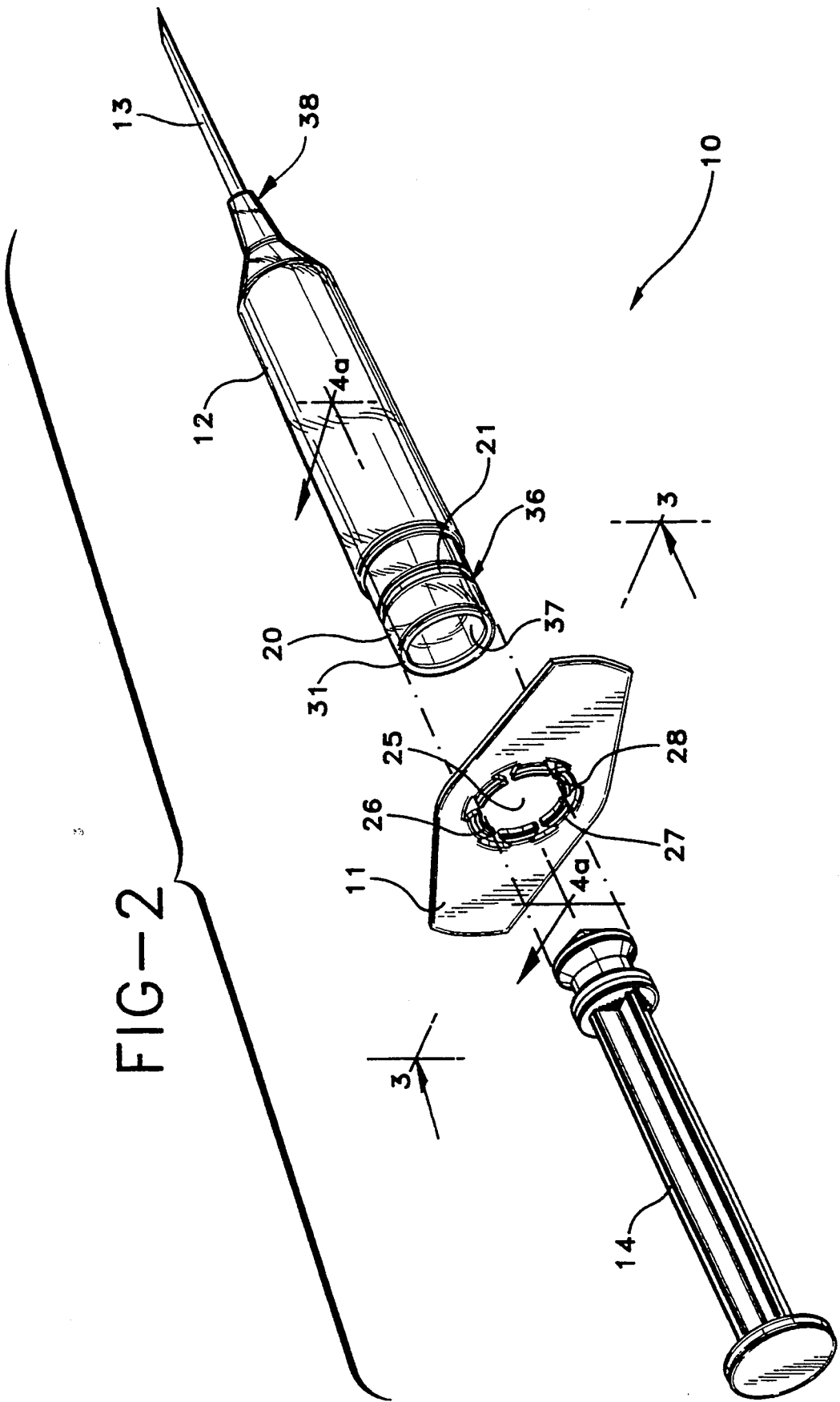
FIG. 2 is an exploded perspective view of the syringe assembly of FIG. 1.
Figure 4A:
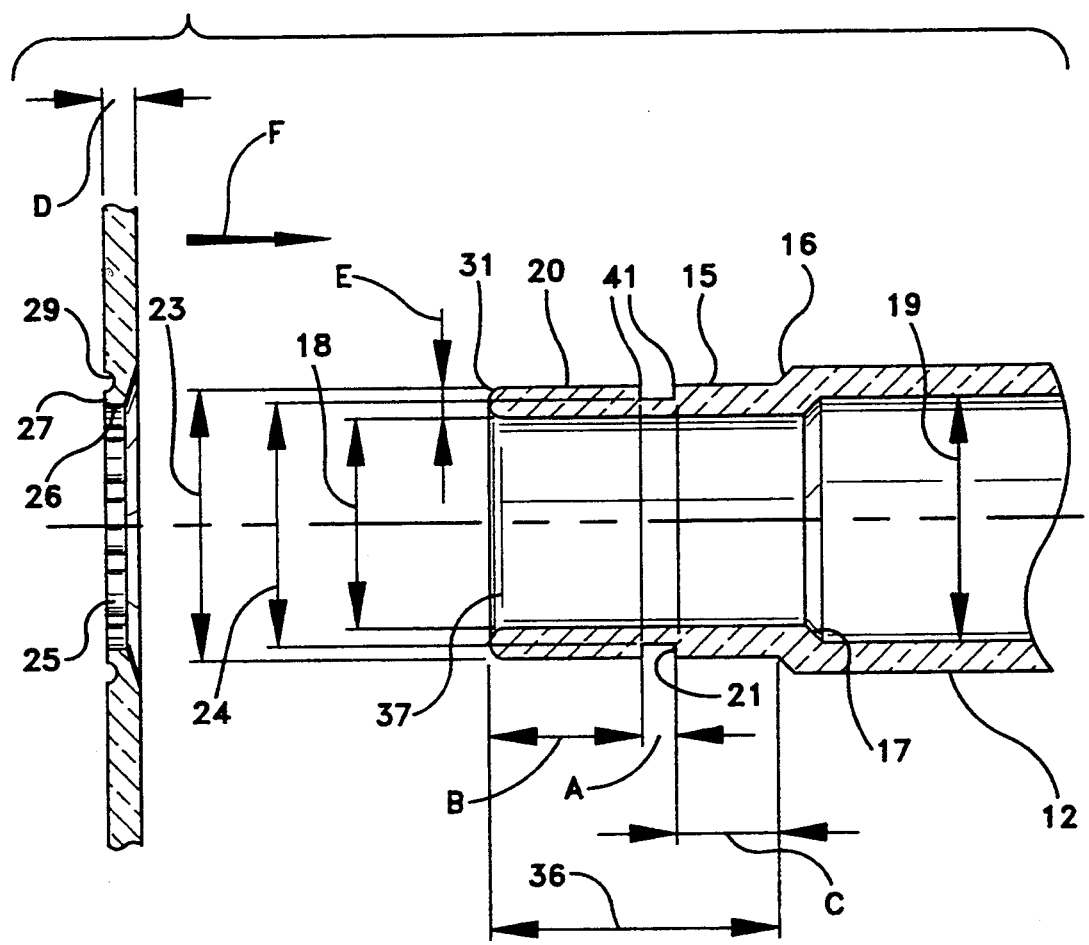
FIGS. 4a, 4b and 4c are enlarged partial cross-sectional views of the syringe assembly of FIG. 1 taken along the line 4—4, showing the finger flange aligned but unmounted (4a), partially mounted (4b) and fully mounted and engaged (4c).

As best illustrated in FIGS. 2 and 4a, said barrel 12 includes a cylindrical barrel portion 35, and a needle assembly 13 located at a distal tip 38 having a passage therethrough fluidly communicative with the bore of cylindrical barrel portion 35. Needle assembly 13 has a lumen therethrough in fluid communication with the passage of tip 38. Assembly 13 may be detachable using one of the common hub arrangements such as a luer lock, luer slip or the like. Alternatively, assembly 13 may be fixedly attached to tip 38. Barrel 12 further includes a proximal portion 36 having an internal opening 37 to receive said plunger assembly 14 and an external portion comprising a first portion 20 including a relieved corner 31, a second portion 21 including a circumferential groove having relieved corners 41, a third portion 15 and a return to full dimension step 16 demarcating the change from said proximal portion 36 to cylindrical barrel portion 35. Located internally within the barrel opposite said step 16 is an internal step 17 wherein a transition is made from a proximal portion 36 having a diameter 18 to said cylindrical barrel portion 35 having a larger diameter 19. A difference between said smaller proximal portion diameter 18 to said cylindrical barrel diameter 19, provides said step 17, which serves as a retention indicator for demarcating the end of useful travel of plunger assembly 14 within cylindrical portion 35 of barrel assembly 12.

Figure 3:
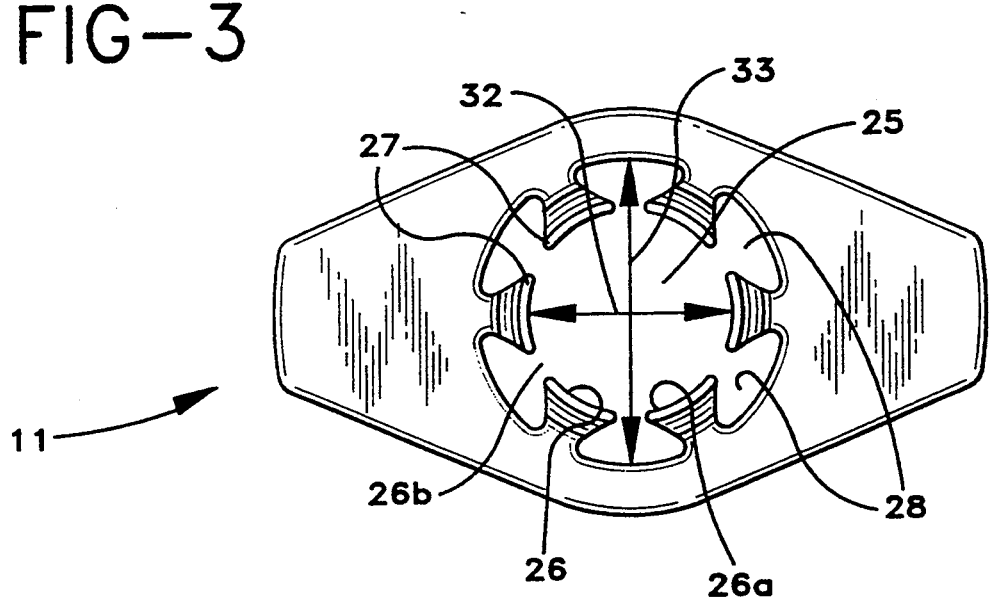
FIG. 3 is a top plan view of the finger flange of the present invention.

As best illustrated in FIG. 3, the finger flange 11 comprises an integrally formed structure having an opening 25 sized to fit with an interference over first portion 20 and conjugate with second portion 21 with interference. Opening 25 has a circumference 26 defined by a plurality of inwardly facing cantilevers 27 having an area of reduced thickness as flex points 29 and recesses 28 therebetween. Circumference 26 thereby comprises two components, cantilever surfaces 26a alternating with spaces 26b from said recesses 28. A diameter 32 of opening 25 at cantilever surfaces 26a is about 8–16 mm less than a diameter 33 at recesses 28, preferably 12 mm less than diameter 33.

Flange 11 is preferably injection molded from a resin selected from the group comprising: polypropylene, polycarbonate, polyamide, polystyrene, polyvinylchloride and acrylonitrile/butadiene/styrene, preferably polypropylene. Barrel 12 can be formed from metal, glass or thermoplastic, with glass being preferred.

Figure 4B:
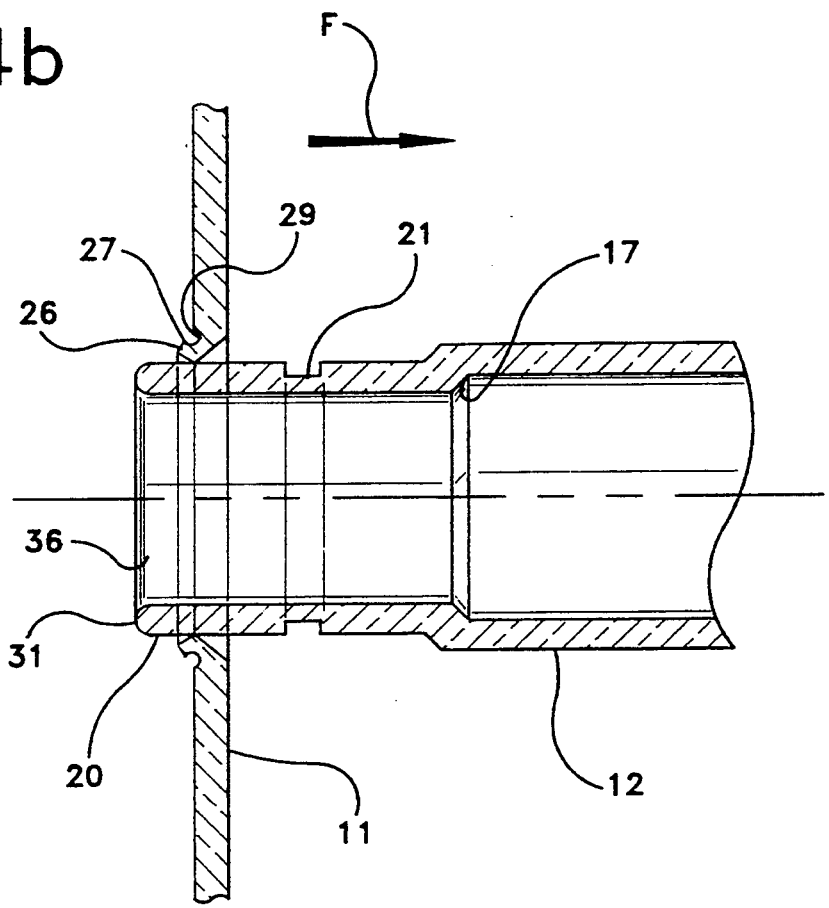
Figure 4C:
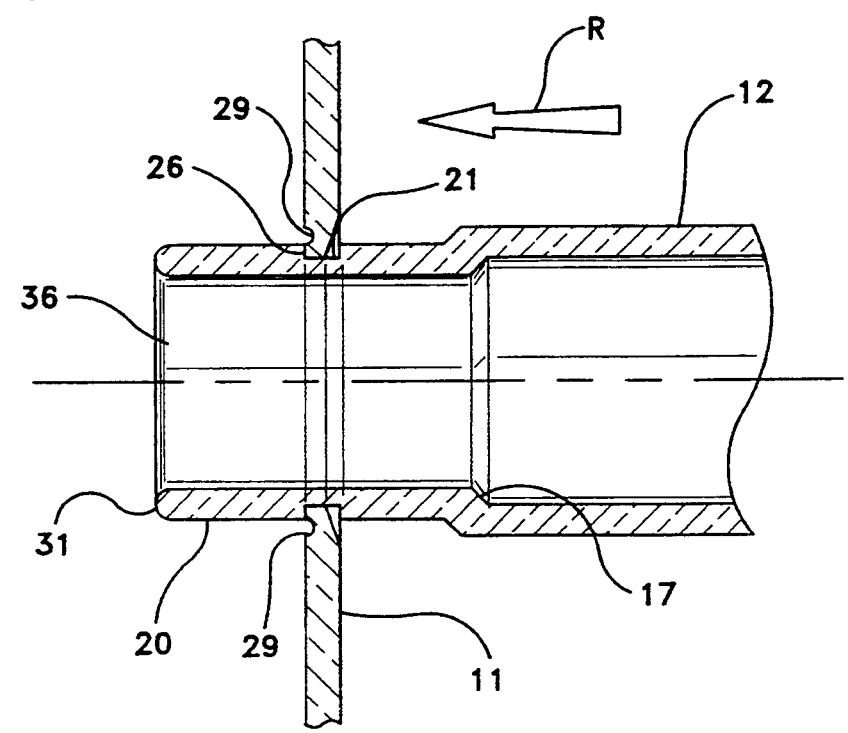

Referring to FIGS. 4a, 4b and 4c, proximal portion 36 of barrel 12 is shown with flange 11 in three different positions respectively: 4a) prior to placement; 4b) partially mounted; and 4c) fully mounted in conjugation with second portion 20. An installation force F is required to cause cantilevers 27 of flange 11 to deflect and move onto first portion 20. Corner 31 of first portion 20 is relieved by a chamfer or radius to aid in placing opening 25 of flange 11 onto first portion 20. FIG. 4c shows cantilevers 27 of flange 11 fully seated in second portion 21 of proximal end 36 after movement by force F over first portion 20.

As best illustrated in FIGS. 3 and 4a, an interference of 0.8 to 1.1 mm is present between cantilever 27 of opening 25 of flange 11 having diameter 32, and first portion 20 having a diameter 23. A diametric interference of 0.4 to 0.9 mm is present with cantilever 27 and second portion 21 having a diameter 24. The difference in diameters 23 and for first portion 20 and second portion 21, respectively, is 0.25 to 0.55 mm, preferably 0.4 mm. A width A of second portion 21 is 2 to 3 mm, preferably 2.2 mm to 2.4 mm. A width B of first portion 20 is 0.5 to 1.5 mm, preferably 1.0 mm. A width C of a third portion 15 is 0.5 to 1.5 mm, preferably 1.0 mm. A relief is present at corners 41 of second portion 21 to assist movement of cantilever 27 into second portion 21 with force F. Cantilever 27 of flange 11 has a thickness D of 2.2 to 2.7 mm, preferably 2.5 mm. Thus the width interference between cantilevers 27 and second portion 21 is preferably 0.1 mm to 0.3 mm. One skilled in the art will recognize that these preferred interferences are illustrative and apply to the preferred embodiment wherein the flange material is polyamide and the barrel is glass. Further, the interferences are preferred only for these general dimensional relationships. As the barrel and flange dimensions become larger or smaller, or when other materials are used, one skilled in the art will recognize that the interference relationships may change.

When flange 11 is fully positioned at second portion 21, a removal force R is required to move flange 11 from second portion 21 back to first portion 20 and further to entirely remove it from barrel 12. The design of cantilever 27 having flex points 29, in conjugation with second portion 21 with said interference is such that said removal force R is greater than installation force F, thus providing for enhanced functional utility for finger flange 11. Additionally, the several design features of central opening 25 having cantilevers 27, recesses 28 and flex point 29 conjugating with second portion 21 having width interference and radial interference serve to position finger flange 11 upon proximal portion 36 of barrel 12 to resist removal force R. Further, by having recesses 28 and flex points 29, any stresses generated by flange 11 upon proximal portion 36 of barrel 12 are uniformly and compliantly spread over the entire area of second portion 21 because of both the compliant nature of the plastic resin used to mold flange 11 and its unique design. Thus problems are avoided associated with the prior art designs having clamping stress and hoop stress which are more sensitive to dimensional variations. Further, the design allows installation force F to be low for easy assembly, while having high removal force R to ensure flange utility when performing an injection with syringe 10. Flange 11 substantially reduces breakage of a glass barrel 12 by serving as a compliant shock absorber if the syringe is dropped or falls during use.

The syringe assembly can be placed in a microorganism resistant package formed from materials known to the art and exposed to a sterilizing environment. This sterilization after packaging allows supply and storage of sterile syringe assemblies. Alternatively, the assemblies can be supplied unassembled and nonsterile or sterile to a user who would assemble, fill and sterilize them as required.

An additional benefit of separately manufacturing flange 11 from barrel 12 is the ability to change the external shape of finger flange 11 to meet particular application requirements, such as a special design to specifically mount the syringe in an particular apparatus. Further, barrel 12 can be provided without any finger flange, but having the hereinabove described design of proximal portion 36 of barrel 12 available for removably interlocking with apparatus designed to accept it. Another advantage would be the ability to complete assembly, filling, packaging and sterilization without mounting a flange, the flanges being included as a compact addition, thus greatly reducing the space requirements required for a given number of syringes. Since the flanges are easily mounted on the barrel, they could be placed on the barrel by the ultimate user as required.

Thus, the design of syringe assembly 10 having flange 11 provides an advance over the prior art of syringe assembly design.

What is claimed is:

1. A syringe assembly comprising:
    a hollow cylindrically shaped barrel having an internal side defining a bore, an external side, a distal end and a proximal end, said proximal end being open to accept a plunger assembly slidably within said bore, said external side having a first portion at said proximal end, a second portion adjacent to said first portion and a third portion adjacent to said second portion, said second portion including a circumferential groove defining a diameter which is smaller than a diameter defined by said first portion and a diameter defined by said third portion, said barrel having a tip at said distal end having a passageway therethrough in fluid communication with said bore;
    a finger flange having an opening, said opening having a diameter defined by a plurality of inwardly facing cantilevers having recesses therebetween; and
    said flange being held by said barrel so that said cantilevers are at least partially positioned in said circumferential groove, said flange opening diameter being smaller than said diameter of said first and third portions of said barrel, said cantilevers having a thickness greater than a width of said circumferential groove so that when said cantilevers are positioned in said groove a width interference exists.

2. The syringe assembly of claim 1 wherein said flange opening diameter, before said flange is positioned on said second portion, is smaller than said diameter of said circumferential groove so that when said cantilevers are positioned in said groove a diametric interference exists.

3. A syringe assembly comprising:
    a hollow cylindrically shaped barrel having an internal side defining a bore, an external side, a distal end and a proximal end, said proximal end being open to accept a plunger assembly slidably within said bore, said external side having a first portion at said proximal end, a second portion adjacent to said first portion and a third portion adjacent to said second portion, said second portion including a circumferential groove defining a diameter which is smaller than a diameter defined by said first portion and a diameter defined by said third portion, said barrel having a tip at said distal end having a passageway therethrough in fluid communication with said bore;
    a finger flange having an opening, said opening having a diameter defined by a plurality of inwardly facing cantilevers having recesses therebetween; and
    said flange being held by said barrel so that said cantilevers are at least partially positioned in said circumferential groove, said flange opening diameter being smaller than said diameter of said first and third portions of said barrel, said flange opening diameter, before said flange is positioned on said second portion, is smaller than said diameter of said circumferential groove, and said cantilevers have a thickness greater than a width of said circumferential groove, so that when said cantilevers are positioned in said groove, said diametric interference and said width interference between said circumferential groove and said cantilevers provide that a force for moving said finger flange distally for installation of said flange onto and over said first portion to engage said cantilevers with said groove is less than a proximal force for removal of said cantilevers from said groove.

4. The syringe assembly of claim 3 wherein said cantilevers have a flex point means for facilitating deflection of said cantilevers to favor a direction for deflection, so that said cantilevers' flexure in a proximal, with respect to said flange, direction is easier than a flexure in a distal direction so that the force for installation is less than the force required to remove said cantilevers from said second portion onto said first portion.

5. The syringe assembly of claim 4, wherein said flex point means includes an area of reduced thickness in said cantilevers.

6. A syringe assembly comprising:
    a hollow cylindrically shaped barrel having an internal side defining a bore, an external side, a distal end and a proximal end, said proximal end being open to accept a plunger assembly slidably within said bore, said external side having a first portion at said proximal end, a second portion adjacent to said first portion and a third portion adjacent to said second portion, said second portion including a circumferential groove defining a diameter which is smaller than a diameter defined by said first portion and a diameter defined by said third portion, said barrel having a tip at said distal end having a passageway therethrough in fluid communication with said bore;

a finger flange having an opening, said opening having a diameter defined by a plurality of inwardly facing cantilevers having recesses therebetween; and said flange being held by said barrel so that said cantilevers are at least partially positioned in said circumferential groove, said flange opening diameter being smaller than said diameter of said first and third portions of said barrel, said cantilevers having a thickness greater than a width of said circumferential groove so that when said cantilevers are positioned in said groove a width interference exists and said first portion has a proximal relieved edge to facilitate movement of said cantilevers over said first portion during installation of said flange onto said barrel.

7. The syringe assembly of claim 6 wherein said cantilevers have a flex point means for facilitating deflection of said cantilevers to favor a direction for deflection, so that said cantilevers' flexure in a proximal, with respect to said flange, direction is easier than a flexure in a distal direction so that the force for installation is less than the force required to remove said cantilevers from said second portion onto said first portion.

8. The syringe assembly of claim 7 wherein said flex point means includes an area of reduced thickness in said cantilevers.

* * * * *